(12) United States Patent
Zhang et al.

(10) Patent No.: US 9,642,832 B2
(45) Date of Patent: May 9, 2017

(54) USE OF ATRACTYLENOLIDE COMPOUND OR ITS DERIVATIVES AND A MEDICAMENT FOR INHIBITING PLATELET AGGREGATION

(71) Applicant: No. 3 People Hospital Affiliated to Shanghai Jiaotong University School of Medicine, Shanghai (CN)

(72) Inventors: Junfeng Zhang, Shanghai (CN); Yizhu Chen, Shanghai (CN)

(73) Assignee: NO. 9 PEOPLE HOSPITAL AFFILIATED TO SHANGHAI JIAOTOG UNIVERSITY SCHOOL OF MEDICINE, Shanghai (CN)

( * ) Notice: Subject to any disclaimer, the term of this patent is extended or adjusted under 35 U.S.C. 154(b) by 0 days.

(21) Appl. No.: 14/908,089

(22) PCT Filed: Apr. 16, 2015

(86) PCT No.: PCT/CN2015/076743
§ 371 (c)(1),
(2) Date: Jan. 27, 2016

(87) PCT Pub. No.: WO2016/090800
PCT Pub. Date: Jun. 16, 2016

(65) Prior Publication Data
US 2016/0324825 A1 Nov. 10, 2016

(30) Foreign Application Priority Data

Dec. 9, 2014 (CN) .......................... 2014 1 0751966
Dec. 9, 2014 (CN) .......................... 2014 1 0752500

(51) Int. Cl.
*A61K 31/365* (2006.01)
*A61K 9/08* (2006.01)

(52) U.S. Cl.
CPC .............. *A61K 31/365* (2013.01); *A61K 9/08* (2013.01)

(58) Field of Classification Search
CPC ................................. A61K 31/365; A61K 9/08
See application file for complete search history.

(56) References Cited

PUBLICATIONS

Peng, (Research progress on the composition of Atractylodes marocephala Koidz lactones and its pharmacological effects, China Pharmacy, vol. 23, No. 39, Dec. 31, 2012 (Dec. 31, 2012), pp. 3732-3734, English translation is used here in the rejection, original document is also filed.*

(Continued)

*Primary Examiner* — Savitha Rao
(74) *Attorney, Agent, or Firm* — Panitch Schwarze Belisario & Nadel LLP

(57) ABSTRACT

A medicament for inhibiting platelet aggregation, comprising atractylenolide compound or its derivatives, wherein the said atractylenolide compound has the following structural formula shown in formula (I), wherein R1 represents H or C1-C10 linear or branched alkyl, R2 represents H or C1-C10 linear or branched alkyl, and R3 represents H or hydroxyl. Use of atractylenolide compound shown in formula (I) or its derivatives in the manufacture of a medicament for inhibiting platelet aggregation. The medicament for inhibiting platelet aggregation of the present application has good efficacy without toxic-and-side effect, lower tendency of tolerance, convenient to take and applicable for preventing or treating diseases caused by high platelet aggregation rate.

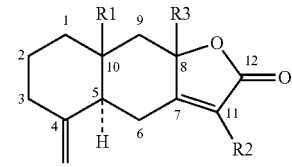

14 Claims, 4 Drawing Sheets

(56) References Cited

PUBLICATIONS

Wang et al. (European Journal of Pharmacology, 612, 2009, pp. 143-152).*
Nasu et al. (Biol. Pharma. Bull. vol. 32 (5), 2009, pp. 856-860)).*
Wagner et al. (Arterisclero Thromb Vasc Biol, 2003, pp. 2131-2137).*
Chen et al, "Atractylodes lactone compounds inhibit platelet activation," Platelets, Early Online, pp. 1-9 (Aug. 25, 2016), published online: http://dx.doi.org/10.1080/09537104.2016.1209477.

* cited by examiner

Resting human plt    DMSO + plt    Atractylenolide II 5uM    Atractylenolide II 10uM Resting human plt    DMSO + plt    Atractylenolide III 5uM    Atractylenolide III 10uM

USE OF ATRACTYLENOLIDE COMPOUND OR ITS DERIVATIVES AND A MEDICAMENT FOR INHIBITING PLATELET AGGREGATION

CROSS REFERENCE TO RELATED APPLICATIONS

This application is the National Phase application under 35 U.S.C. §371 of International Application No. PCT/CN2015/076743, filed Apr. 16, 2015, which claims the benefit of priority from Chinese application CN 201410751966.9, filed Dec. 9, 2014, and Chinese application CN 201410752500.0, filed Dec. 9, 2014, each of which is hereby incorporated by reference in its entirety for all purposes as if put forth in full below.

FIELD OF THE INVENTION

The present invention relates to the pharmaceutical technical field, especially relates to the use of atractylenolide compound or its derivatives in the manufacture of a medicament for inhibiting platelet aggregation and the medicament for inhibiting platelet aggregation.

BACKGROUND OF THE INVENTION

In modern medical science, it is deemed that the formation of thrombus has a certain relationship with the exorbitant platelet aggregation rate.

Thrombus originates from the local coagulation mechanism, which is covered by proliferative endotheliocyte after hyper-thrombosis of endarterium surface, while lipides and other active substances, which are released by the lysis of platelet and leukocyte, enter the mural thrombus of artery to form the atheromatous plaque gradually. Subsequent researchers find out that the disease originates from the injury in arterial tunica intima, then platelet activating factor (PAF) increases and platelets adhere and aggregate here, subsequently microthrombus is formed by fibrin deposition. Some active substances are released by the platelet after their aggregation, wherein the thromboxane A2 (TXA2) can offset the effect of platelet depolymerization and vasodilatation produced by the prostacycline (PGI2) that is synthesized by blood vessel wall and thus promotes further platelet aggregation and vasoconstriction, the platelet derived growth factor can stimulate the proliferation and contraction of smooth muscle cells and make them move towards tunica intima, 5-serotonin and fibroblast growth factor can stimulate fibroblast smooth muscle cells and endotheliocyte to produce epinephrine and ADP (adenosine diphosphate) and thus promote further platelet aggregation, Factor VIII causes the further adhesion of platelet, platelet factor 4 can make the blood vessels constrict, PAI (plasminogen activator inhibitor) inhibits the thrombolysis of thrombus. These substances aggravate the injury of endotheliocyte, which subsequently causes the following results that are all in favor of the formation of scleratheroma: LDL (low-density lipoprotein) enters tunica intima and even beneath it, monocytes aggregate in tunica intima and develop into foam cells, smooth muscle cells proliferate and move into tunica intima to phagocytose the lipids, and endothelial cells proliferate.

There are coagulation system and anticoagulation system in human blood. Under normal circumstances, these two systems keep a dynamic balance to ensure the normal flow of blood in blood vessels, which means thrombus wouldn't be formed. Under special circumstances, e.g. blood vessels have injury such as vascular sclerosis and hemadostenosis, cold weather, excessive sweating, hypotension, insufficient water drinking, etc., blood flows slowly and becomes concentrated and viscous, leading to hypercoagulation or impaired anticoagulation, and subsequently the abovementioned balance is disrupted which results in a "thrombophilic state". Thromboembolic diseases may occur everywhere of blood vessels, wherein thrombus flows in blood vessels along with blood. If thrombus stays in cerebral artery vessels and hinders the normal blood flow of the cerebral artery, it is referred to as cerebral thrombus which thereby causes ischemic stroke attacks, and if it blocks coronary artery vessels of the heart, it causes myocardial infarction, as well as arterial thrombosis in lower extremity, deep venous thrombosis in lower extremity and pulmonary embolism, etc.

When it onsets, most thrombosis will cause severe symptoms, such as hemiplegia and aphasia for cerebral infarction, intense angina in precordial region for myocardial infarction, severe chest pain, dyspnoea, hemoptysis and other symptoms caused by pulmonary infarction, pain in legs or coldness and intermittent claudication, etc. in case of thrombosis in lower extremity. Extremely severe heart infarction, cerebral infarction and pulmonary infarction can even result in sudden death. Whereas thrombosis may have no obvious symptoms sometimes, taking the commonly observed deep venous thrombosis in lower extremity for example, patients suffering this disease just feel sour and swollen legs, and most of them often consider it as the result of fatigue or cold, and subsequently miss the optimal treatment timing. It is particularly unfortunate that many doctors often misdiagnose it as other diseases. When typical edema of lower extremity develops, the treatment of the disease will be difficult and sequela will be left. The formation of thrombus will often result in the aforesaid severe consequences, but up to now there hasn't been a drug with high efficacy without toxic-and-side effects for use in treating or preventing thrombosis.

Atractylenolide compounds, e.g. atractylenolide II, atractylenolide III, etc., derive from extracts of dried roots of compositae plant *Atractylodes macrocephala* Koidz. In researches of prior art, atractylenolide compounds have anti-inflammatory and antitumor effects together with properties of regulating gastrointestinal peristalsis and promoting the absorption of nutrients. Nonetheless, up to now, the effect of inhibiting platelet aggregation of atractylenolide compounds has not been reported yet.

SUMMARY OF THE INVENTION

In order to solve the technical problem of lacking effective and safe drugs used for the treatment and prevention of thrombus currently, the present invention provides a drug comprising atractylenolide compound or its derivatives having the effect of anti-platelet aggregation, wherein the drug has a simple composition and is composed by active ingredients of natural medicinal materials or extracts thereof. This drug has high efficacy without toxic-and-side effects, lower tendency of tolerance, convenient to take and generally applicable for preventing or treating symptoms like viscous blood and thrombus caused by exorbitant platelet aggregation rate.

In one aspect of the present invention, it provides a medicament for inhibiting platelet aggregation comprising atractylenolide compound or its derivatives, wherein said atractylenolide compound has the structural formula shown in following formula (I):

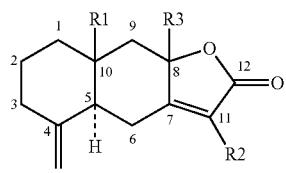

(I)

wherein R1 represents H or C1-C10 linear or branched alkyl, R2 represents H or C1-C10 linear or branched alkyl, and R3 represents H or hydroxyl.

Preferably, said atractylenolide compound has the structural formula shown in following formula (II):

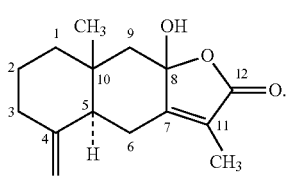

(II)

The structural formula shown in formula (II) is the chemical structural formula of atractylenolide M. Preferably, said atractylenolide compound has the structural formula shown in following formula (III):

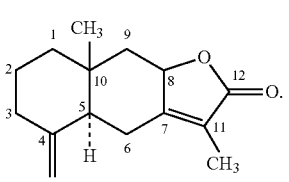

(III)

The structural formula shown in formula (M) is the chemical structural formula of atractylenolide I. Preferably, said derivatives of atractylenolide compound have the structural formula shown in following formula (IV):

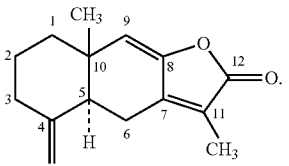

(IV)

The structural formula shown in formula (IV) is the chemical structural formula of atractylenolide II.

Said medicament is present in the dosage forms including tablet, granule, capsule, patch or injection.

Said C1-C10 alkyl is preferably C1-C8 alkyl, more preferably C1-C6 alkyl, such as methyl, ethyl, n-propyl, iso-propyl, n-butyl, iso-butyl, tert-butyl, n-pentyl, iso-pentyl, n-hexyl, iso-hexyl.

Wherein, said alkyl can be linear alkyl or branched alkyl, preferably linear alkyl.

The derivatives of atractylenolide compound in the present invention refer to a kind of substances having similar chemical structures to atractylenolide, which are obtained by the derivatization and modification of functional groups in the chemical structural formula of atractylenolide, such as ester bond, epoxy ring, carbon-carbon double bond, etc. For example, the modification of ester bond is achieved by ester hydrolysis of atractylenolide under acidic or alkaline condition. The hydrolysis of epoxy ring is occurred under acidic or alkaline condition.

The medicament for inhibiting platelet aggregation of the present invention also comprises pharmaceutically acceptable excipients.

Preferably, said excipients include one or more of the following: solvent, propellent, solubilizer, cosolvent, emulsifier, colorant, adhesive, disintegrant, filling agent, lubricant, wetting agent, osmotic pressure regulator, stabilizer, glidant, corrigent, preservative, suspending agent, coating material, fragrance, anti-adhesive, chelating agent, penetration enhancer, pH regulator, buffering agent, plasticizer, surfactant, foaming agent, defoaming agent, thickening agent, clathrate agent, humectant, absorbent, diluent, flocculant and deflocculant, filter aid agent, or releasing blocker.

In another aspect of the present invention, it provides the use of atractylenolide compound or its derivatives shown in formula (I) in the manufacture of a medicament for inhibiting platelet aggregation,

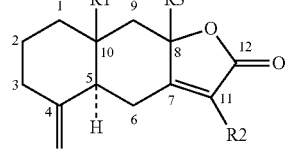

(I)

Wherein, R1 represents H or C1-C10 linear or branched alkyl, R2 represents H or C1-C10 linear or branched alkyl, and R3 represents H or hydroxyl.

Said medicament for inhibiting platelet aggregation includes the medicament that is used for treating or preventing viscous blood, cerebral infarction, myocardial infarction, pulmonary embolism, arterial thrombosis in lower extremity and deep venous thrombosis in lower extremity.

The medicament for inhibiting platelet aggregation of the present invention has a good efficacy while no toxic and side effect. As shown by the comparative experiment with current medicament for inhibiting platelet aggregation, acetylsalicylic acid, that the atractylenolide compound or its derivatives of the present invention have a significant effect of inhibiting platelet aggregation, and is suitable to prevent or treat diseases caused by exorbitant platelet aggregation and have a broad prospect in application.

BRIEF DESCRIPTION OF THE DRAWINGS

Below is a detailed description of the present invention in combination with drawings and specific examples.

DETAILED DESCRIPTION OF THE INVENTION

Taking atractylenolide II and atractylenolide III for example, the effect of atractylenolide compound or its derivatives of the present invention on inhibiting platelet aggregation is illustrated in details.

EXAMPLE 1

Effect of Atractylenolide II on Platelet Aggregation Inhibition in Platelet Aggregation Test I. Materials and Preparation
Atractylenolide II, dissolved in DMSO.
II. Experimental Procedure
Platelet Aggregation Test
(1) Preparation of platelets: human blood plasma with high concentration of platelets is used to prepare platelets counting $3\times10^8$/mL, which are placed in a water bath of 37° C.
(2) Concentration gradient of compound atractylenolide final concentrations of the compound in 300 uL platelets are respectively 0.1 μM, 0.5 μM, 1 μM, 5 μM, 10 μM.

Figure 1:
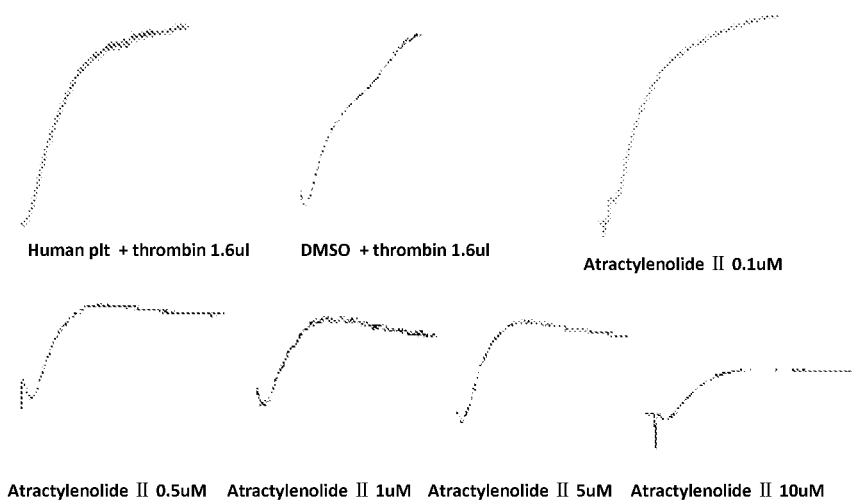
FIG. 1 shows the experimental results of in vitro platelet aggregation inhibition by atractylenolide II in Example 1.

The compound is incubated in platelets for 3 mins before the experiment, and resting and DMSO are included in the experiment as control groups. Thrombin is used as stimulant. The aggregation curve and aggregation rate are obtained by the platelet aggregation test instrument.
References:
Weng Z, Li D, Zhang L, et al. PTEN regulates collagen-induced platelet activation. *Blood.* 2010; 116(14): 2579-2581.
Liu J, Jackson C W, Gruppo R A, Jennings L K, Gartner T K. The beta3 suunit of the integrin alphaIIbbeta3 regulates alphaIIb-mediated outside-in signaling. *Blood.* 2005; 105 (11):4345-4352.
(3) Experimental results (see FIG. 1):
It can be seen from the above experimental results that: atractylenolide II has an effect of inhibiting platelet aggregation and the high concentration of atractylenolide II has a more significant effect.

EXAMPLE 2

Effect of Atractylenolide III on Platelet Aggregation Inhibition in Platelet Aggregation Test I. Materials and Preparation
Atractylenolide III, dissolved in DMSO.
II. Experimental Procedure
Platelet Aggregation Test
(1) Preparation of platelets: human blood plasma with high concentration of platelets is used to prepare platelets counting $3\times10^8$/mL, which are placed in a water bath of 37° C.
(2) Concentration gradient of compound atractylenolide III; final concentrations of the compound in 300 uL platelets are respectively 0.1 μM, 0.5 μM, 1 μM, 5 μM, 10 μM.

Figure 2:
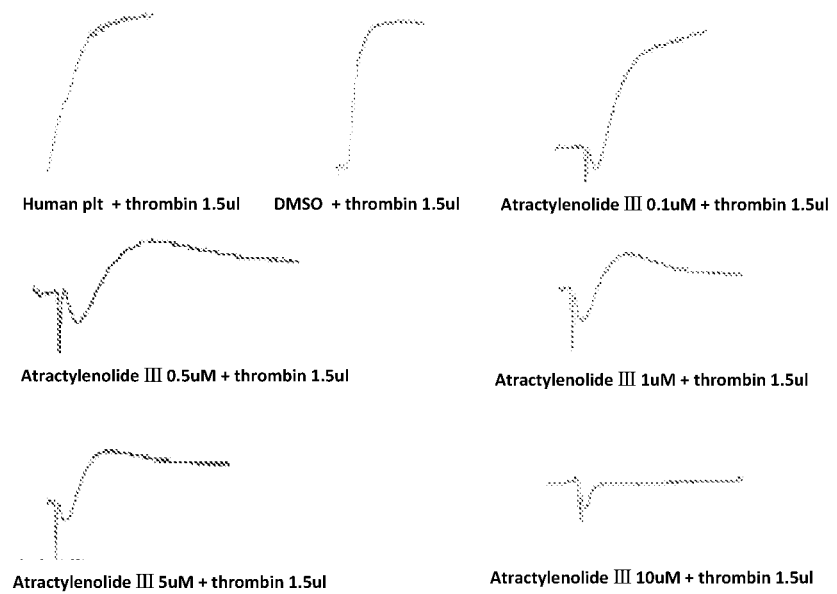
FIG. 2 shows the experimental results of in vitro platelet aggregation inhibition by atractylenolide Ill in Example 2.

The compound is incubated in platelets for 3 mins before the experiment, and resting and DMSO are included in the experiment as control groups. Thrombin is used as stimulant. The aggregation curve and aggregation rate are obtained by the platelet aggregation test instrument.
(3) Experimental results (see FIG. 2):
It can be seen from the above experimental results that: atractylenolide III has an effect of inhibiting platelet aggregation and the high concentration of atractylenolide III has a more significant effect.

EXAMPLE 3

Influence of Atractylenolide II in Platelet Spreading Test

Figure 3:
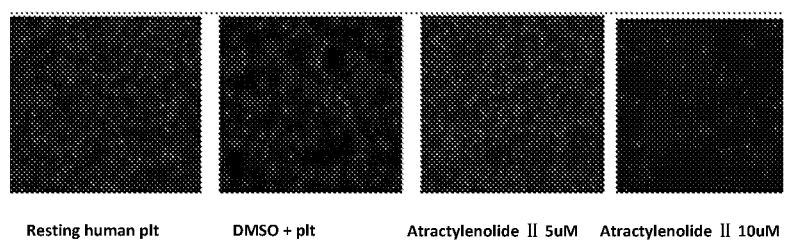
FIG. 3 shows the oil immersion lens observation of the effect of atractylenolide II on platelet spreading in Example 3.

Platelet Spreading Test
(1) Preparation of platelets: use the same method as abovementioned to prepare platelets counting $3\times10^7$/mL.
(2) Concentration gradient of compound atractylenolide II: final concentrations of the compound in 100 uL platelets are respectively 1 μM, 5 μM, 10 μM. The compound is incubated in platelets for 3 mins. The platelets treated by the drug are spread on fibrin (40 μg/mL). After Staining by the fluorescent antibody phalloidin, the spreading of platelets are observed under the 100× oil immersion lens.
References:
Chen X, Zhang Y, Wang Y, et al. PDK1 regulates platelet activation and arterial thrombosis. *Blood.* 2013; 121(18): 3718-3726.
(3) Experimental results (see FIG. 3):
The experimental results show that atractylenolide II has an influence on platelet spreading.

EXAMPLE 4

Influence of Atractylenolide III in Platelet Spreading Test

Figure 4:
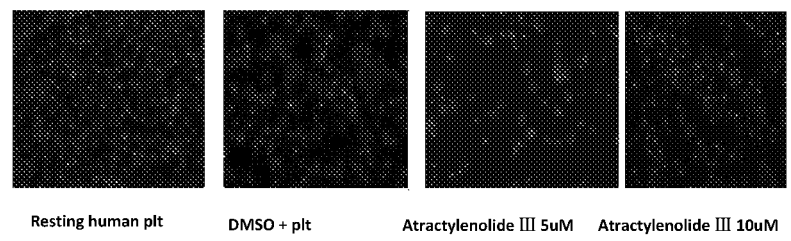
FIG. 4 shows the oil immersion lens observation of the effect of atractylenolide Ill on platelet spreading in Example 4.

Platelet Spreading Test
(1) Preparation of platelets: use the same method as abovementioned to prepare platelets counting $3\times10^7$/mL.
(2) Concentration gradient of compound atractylenolide III; final concentrations of the compound in 100 uL platelets are respectively 1 μM, 5 μM, 10 μM. The compound is incubated in platelets for 3 mins. The platelets treated by the drug are spread on fibrin (40 μg/mL). After staining by the fluorescent antibody phalloidin, the spreading of platelets is observed under the 100× oil immersion lens.
(3) Experimental results (see FIG. 4):
The experimental results indicate that atractylenolide III has an influence on platelet spreading.

EXAMPLE 5

Western Blotting Test on Phosphorylation Levels of Related Molecules During the Inhibition of Platelet Aggregation by Atractylenolide II After acquiring the aggregation curve in Example 1, platelet protein samples (2×SDS loading protein lysis buffer) are collected, and tested by Western blotting for phosphorylation levels of related molecules.

Figure 5:
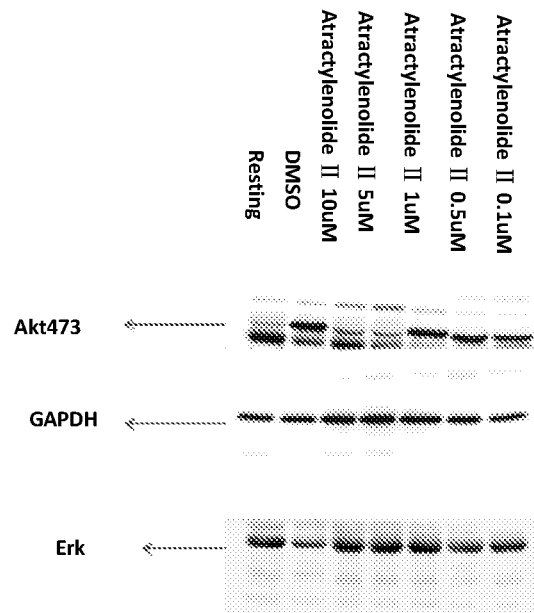
FIG. 5 shows the testing results of Western blotting in Example 5.

Experimental results (see FIG. 5) are as follows:

Testing the phosphorylation levels of related molecules in the signal pathway using Western blotting, when the PI3K/Akt signal pathway is activated, the Akt molecule is activated via phosphorylation, which leads to the activation of downstream enzymes, kinases, transcription factors (e.g. GSK3), etc. Subsequently, platelets are activated to aggregate, and the higher the phosphorylation level of the Akt molecule is, the higher degree the platelets aggregate. The experimental results show that: atractylenolide II affects the phosphorylation level of the Akt molecule, and the influence of concentration variation on phosphorylation level of the Akt molecule is consistent with that on the degree of platelet aggregation.

EXAMPLE 6

Western Blotting Test on Phosphorylation Levels of Related Molecules During the Inhibition of Platelet Aggregation by Atractylenolide III After acquiring the aggregation curve in Example 2, platelet protein samples (2×SDS loading protein lysis buffer) are collected, and tested by Western blotting for phosphorylation levels of related molecules.

Figure 6:
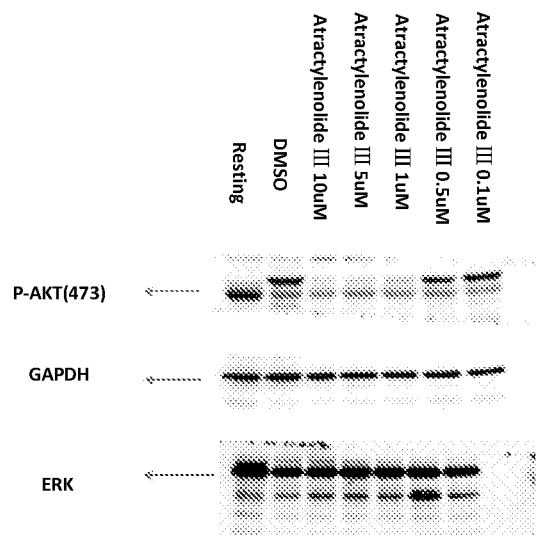
FIG. 6 shows the testing results of Western blotting in Example 6.

Experimental results (see FIG. 6) are as follows:

Testing the phosphorylation levels of related molecules in the signal pathway using Western blotting, when the PI3K/Akt signal pathway is activated, the Akt molecule is activated via phosphorylation, which leads to the activation of downstream enzymes, kinases, transcription factors (e.g. GSK3), etc. Subsequently, platelets are activated to aggregate, and the higher phosphorylation level of the Akt molecule is, the higher degree the platelets aggregate. The experimental results show that: atractylenolide III affects the phosphorylation level of the Akt molecule, and the influence of concentration variation on phosphorylation level of the Akt molecule is consistent with that on the degree of platelet aggregation.

EXAMPLE 7

Comparative Experiments Comparing in vitro Platelet Aggregation Inhibition by Atractylenolide II and Acetylsalicylic Acid (1) Preparation of platelets: use the same method as abovementioned to prepare platelets counting $3\times10^8$/mL.

(2) Acetylsalicylic acid is dissolved in anhydrous ethanol, and diluted into a concentration of 50 mmol/L, it is then stimulated with the thrombin stimulant to observe the platelet aggregation.

Figure 7:
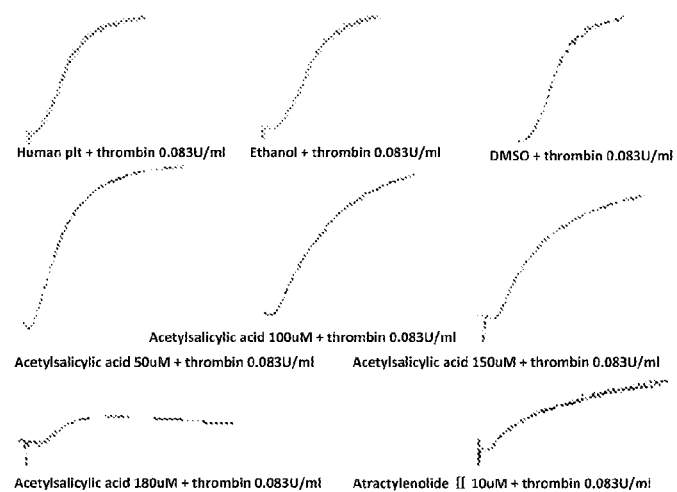
FIG. 7 shows the result of comparative experiments comparing in vitro platelet aggregation inhibition by atractylenolide II and acetylsalicylic acid in Example 7.

Experimental results (see FIG. 7) are as follows:

In the in vitro experiments with identical conditions, acetylsalicylic acid does not show the inhibitory effect yet at a high concentration of 150 µM under the stimulus of thrombin, but atractylenolide II has the effect of inhibiting platelet aggregation at a low concentration (10 µM) in the in vitro experiment.

EXAMPLE 8

Comparative Experiments Comparing in vitro Platelet Aggregation Inhibition by Atractylenolide III and Acetylsalicylic Acid (1) Preparation of platelets: use the same method as abovementioned to prepare platelets counting $3\times10^8$/mL.

(2) Acetylsalicylic acid is dissolved in anhydrous ethanol, and diluted into a concentration of 50 mmol/L, it is stimulated with the thrombin stimulant to observe the platelet aggregation.

Figure 8:
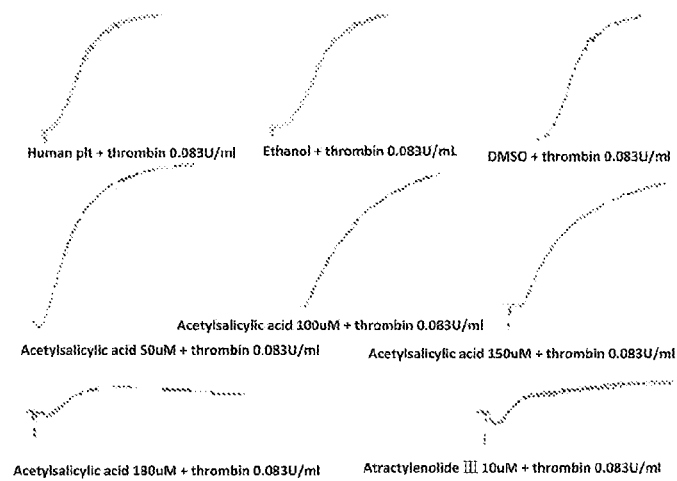
FIG. 8 shows the result of comparative experiments comparing in vitro platelet aggregation inhibition by atractylenolide III and acetylsalicylic acid in Example 8.

Experimental results (see FIG. 8) are as follows:

In the in vitro experiments with identical conditions, acetylsalicylic acid does not show the inhibitory effect yet at a high concentration of 150 µM under the stimulus of thrombin, but atractylenolide III has the effect of inhibiting platelet aggregation at a low concentration (10 µM) in the in vitro experiment.

The aforementioned examples merely illustrate embodiments of the present invention, the description is comparatively concrete and detailed, but it cannot be consequently understood as a limit of the scope of the present invention. It should be pointed out that for persons skilled in the art, many changes and improvements can be made without departing from the conception of the present invention, all of which fall into the protection scope of the present invention. Therefore, for the protection scope of the present invention, the attached claims should prevail.

The invention claimed is:

1. A method for inhibiting platelet aggregation in a subject in need thereof, comprising administering to the subject an isolated atractylenolide compound of formula (I):

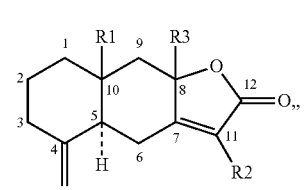

wherein
R1 is methyl;
R2 is methyl; and
R3 is H or hydroxyl.

2. The method of claim 1, wherein the atractylenolide compound is of the formula (II):

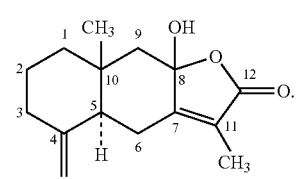

3. The method of claim 1, wherein the atractylenolide compound is of the formula (III):

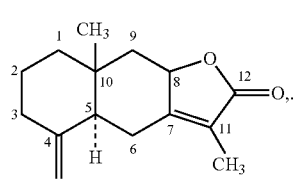

4. The method of claim 1, wherein the atractylenolide compound is administered in a dosage form selected from the group consisting of a tablet, a granule, a capsule, a path and an injection.

5. The method of claim 1, further comprising administering a pharmaceutically acceptable excipient.

6. The method of claim 5, wherein the pharmaceutically acceptable excipient comprises one or more excipients selected from the group consisting of a solvent, a propellant, a solubilizer, a cosolvent, an emulsifier, a colorant, an adhesive, a disintegrant, a filling agent, a lubricant, a wetting agent, an osmotic pressure regulator, a stabilizer, a glidant, a corrigent, a preservative, a suspending agent, a coating material, a fragrance, an anti-adhesive, a chelating agent, a penetration enhancer, a pH regulator, a buffering agent, a plasticizer, a surfactant, a foaming agent, a defoaming agent, a thickening agent, a clathrate agent, a humectant, an absorbent, a diluent, a flocculant, a deflocculant, a filter aid agent, and a releasing blocker.

7. A method for treating a disease caused by high platelet aggregation rate in a subject in need thereof, comprising administering to the subject a pharmaceutical composition comprising a pharmaceutically acceptable excipient and an isolated atractylenolide compound of formula (I):

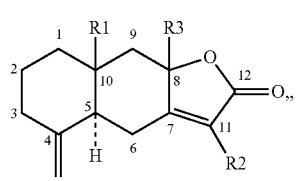

(I)

wherein
R1 is methyl;
R2 is methyl; and
R3 is H or hydroxyl.

8. The method of claim 7, wherein the disease caused by high platelet aggregation rate is viscous blood, cerebral infarction, myocardial infarction, pulmonary embolism, arterial thrombosis in lower extremity and deep venous thrombosis in lower extremity.

9. The method of claim 7, wherein the atractylenolide compound is of formula (II):

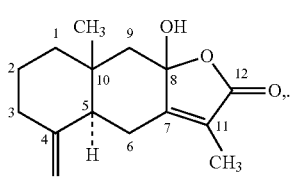

(II)

10. The method of claim 7, wherein the atractylenolide compound is of formula (III):

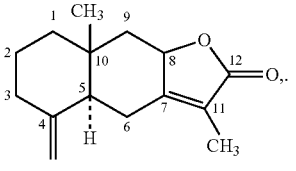

(III)

11. The method of claim 7, wherein the isolated atractylenolide compound is administered in a dosage form selected from the group consisting of a tablet, a granule, a capsule, a path and an injection.

12. A method for treating cerebral infarction, myocardial infarction, or arterial thrombosis in lower extremities caused by high platelet aggregation rate in a subject in need thereof, comprising administering to the subject a pharmaceutical composition comprising a pharmaceutically acceptable excipient and an isolated atractylenolide compound of formula (I):

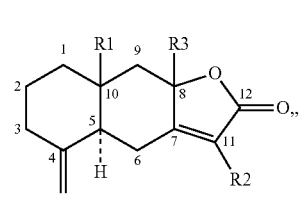

(I)

wherein
R1 is methyl;
R2 is methyl; and
R3 is H or hydroxyl.

13. The method of claim 12, wherein the atractylenolide compound is of formula (II):

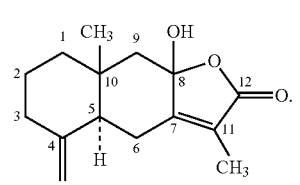

(II)

14. The method of claim 12, wherein the atractylenolide compound is of formula (III):

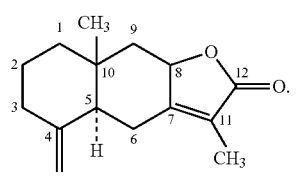

(III)

* * * * *